United States Patent
Hassan et al.

(10) Patent No.: US 8,088,953 B2
(45) Date of Patent: *Jan. 3, 2012

(54) HIGH SHEAR OXIDATION OF CYCLOHEXANE

(75) Inventors: Abbas Hassan, Sugar Land, TX (US); Aziz Hassan, Sugar Land, TX (US); Gregory G. Borsinger, Chatham, NJ (US); Krishnan Viswanathan, Houston, TX (US); Rayford G. Anthony, College Station, TX (US)

(73) Assignee: H R D Corporation, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/628,795

(22) Filed: Dec. 1, 2009

(65) Prior Publication Data

US 2010/0168477 A1    Jul. 1, 2010

Related U.S. Application Data (60) Continuation-in-part of application No. 12/411,660, filed on Mar. 26, 2009, which is a division of application No. 12/138,279, filed on Jun. 12, 2008, now Pat. No. 7,592,493.

(60) Provisional application No. 60/946,584, filed on Jun. 27, 2007.

(51) Int. Cl.
*C07C 45/00* (2006.01)
*C07C 35/08* (2006.01)

(52) U.S. Cl. .................................. 568/376; 568/836
(58) Field of Classification Search .............. 568/376, 568/836

See application file for complete search history.

(56) References Cited

U.S. PATENT DOCUMENTS

| | | | | |
|---|---|---|---|---|
| 5,780,683 | A * | 7/1998 | Greene et al. | 568/358 |
| 5,877,350 | A | 3/1999 | Langer et al. | |
| 5,892,122 | A * | 4/1999 | Ostermaier et al. | 568/357 |
| 6,368,366 | B1 | 4/2002 | Langer et al. | |
| 6,368,367 | B1 | 4/2002 | Langer et al. | |
| 6,383,237 | B1 | 5/2002 | Langer et al. | |
| 7,592,493 | B2 * | 9/2009 | Hassan et al. | 568/836 |
| 2003/0043690 | A1 | 3/2003 | Holl | |
| 2004/0052158 | A1 | 3/2004 | Holl | |
| 2005/0033069 | A1 | 2/2005 | Holl et al. | |

* cited by examiner

*Primary Examiner* — Sikarl Witherspoon (57) ABSTRACT

Disclosed herein is a method for cyclohexane oxidation. The method comprises a) forming a dispersion comprising liquid cyclohexane and an oxidant gas utilizing a high shear device, wherein the dispersion comprises oxidant gas bubbles with a mean diameter of less than about 5 μm, and wherein the high shear device comprises at least one rotor and at least one stator; and b) hydrogenating the dispersion in the presence of a hydrogenation catalyst to form a product comprising cyclohexanol or cyclohexanone. In some embodiments, the oxidant comprises air, oxygen-enriched air, oxygen, or an oxygen-containing gas. In some embodiments, step a) of the method comprises forming the dispersion in the presence of an oxidation catalyst. Also disclosed herein is a system for oxidizing cyclohexane.

10 Claims, 8 Drawing Sheets

HIGH SHEAR OXIDATION OF CYCLOHEXANE

CROSS-REFERENCE TO RELATED APPLICATIONS

The present application is a continuation-in-part of U.S. patent application Ser. No. 12/411,660 filed on Mar. 26, 2009, which is a divisional application of U.S. patent application Ser. No. 12/138,279 filed on Jun. 12, 2008 (now issued as U.S. Pat. No. 7,592,493), which application claims the benefit under 35 U.S.C. §119(e) of U.S. Provisional Patent Application No. 60/946,584 filed Jun. 27, 2007, the disclosures of which are hereby incorporated herein by reference.

STATEMENT REGARDING FEDERALLY SPONSORED RESEARCH OR DEVELOPMENT

Not Applicable.

FIELD OF THE INVENTION

The present invention generally relates to oxidation process of cyclohexane. More particularly, the present invention relates to utilizing high shear in oxidizing cyclohexane.

BACKGROUND

Cyclohexane ($C_6H_{12}$) is a cycloalkane. It is often used as a nonpolar solvent in the chemical industry. Commercially most of cyclohexane produced is converted into cyclohexanone-cyclohexanol mixture (i.e., "KA oil") by catalytic oxidation. A mixture of cyclohexanol and cyclohexanone may be referred to as ketone-alcohol oil, or KA oil. Cyclohexanol comprises the alcohol portion (A); cyclohexanone comprises the ketone (K) portion of the mixture. The cyclohexanone-cyclohexanol mixture (KA oil) is then used as a raw material for the industrial production of adipic acid and caprolactam, both of which are intermediates for nylon production.

Therefore, there is continuing interest in developing new cyclohexane oxidation processes that are efficient and economical.

SUMMARY

In an embodiment, a method is disclosed, comprising a) forming a dispersion comprising liquid cyclohexane and an oxidant gas utilizing a high shear device, wherein the dispersion comprises oxidant gas bubbles with a mean diameter of less than about 5 µm, and wherein the high shear device comprises at least one rotor and at least one stator; and b) hydrogenating the dispersion in the presence of a hydrogenation catalyst to form a product comprising cyclohexanol or cyclohexanone. In some embodiments, the oxidant comprises air, oxygen-enriched air, oxygen, or an oxygen-containing gas. In some embodiments, step a) of the method comprises forming the dispersion in the presence of an oxidation catalyst. In various embodiments, the oxidation catalyst comprises the oxides of vanadium (V), manganese (Mn), nickel (Ni), copper (Cu), zinc (Zn), molybdenum (Mo), zirconium (Zr), or Cerium (Ce) over α-alumina support. In some cases, the oxidation catalyst comprises a soluble transition metal compound. In some further cases, the soluble transition metal compound comprises a cobalt ester of naphthenic acid, octanoic acid, 2-ethylhexanoic acid, or a carboxylic acid. In some embodiments, step a) of the method comprises forming a dispersion comprising the liquid cyclohexane, the oxidant gas, and an oxidation catalyst slurry. In some cases, the high shear device comprises a surface containing an oxidation catalyst. In some embodiments, step a) of the method comprises forming a precursor comprising a cyclohexyl hydroperoxide, a ketal, a acetal, 1,1' oxybiscyclohexane, a cyclohexyl ester of monocarboxylic and dicarboxylic acids, 7-oxabicycloheptane, 2-hydroxycyclohexanone, 2h-pyran-2-one tetrahydro, or 2-oxepanone. In some embodiments, step b) of the method comprises subjecting the dispersion to high shear.

In another embodiment, a system is described, comprising: a high shear device comprising at least one inlet, at least one outlet, and at least one rotor and at least one stator having a minimum clearance therebetween in the range of from 0.5 mm to 2.5 mm; and a reactor comprising at least one inlet and at least one outlet, wherein the at least one reactor inlet is fluidly connected to the at least one outlet of the high shear device; and wherein the reactor is configured to provide hydrogenation reaction conditions. In some embodiments, the high shear device of such a system comprises a surface containing an oxidation catalyst. In some cases, the oxidation catalyst comprises the oxides of vanadium (V), manganese (Mn), nickel (Ni), copper (Cu), zinc (Zn), molybdenum (Mo), zirconium (Zr), or Cerium (Ce). In some embodiments, the system further comprises a distillation system comprising at least one inlet and one outlet, wherein the at least one distillation system inlet is fluidly connected to the at least one outlet of the reactor; and wherein the distillation system is configured to recover a product comprising cyclohexanol or cyclohexanone. In some other embodiments, the system comprises multiple high shear devices connected with one another in series or in parallel or in a combination of in-series and in-parallel configuration. In yet other embodiments, the reactor of the system comprises a fixed bed catalyst.

In a further embodiment, a system for oxidizing cyclohexane is disclosed. The system comprises a high shear device comprising at least one rotor and at least one stator having a minimum clearance therebetween and configured to produce a dispersion of oxidant gas in a solution comprising cyclohexane, the dispersion having an average bubble diameter of less than about 5 µm; and a vessel fluidly connected to an outlet of the high shear device, wherein the vessel comprises apparatus such that contents of the vessel is maintained at a temperature of less than about 160° C. In some embodiments, the high shear device comprises at least two rotors and at least two stators. In some embodiments, the high shear device is adapted to rotate the at least one rotor at a tip speed of at least 5 msec. In some embodiments, the high shear device is adapted to rotate the at least one rotor at a tip speed of at least 20 msec. In some embodiments, the high shear device is configured to produce a localized pressure of at least about 1000 MPa at the tip of the rotor during operation of the high shear device. In some embodiments, the high shear device produces a shear rate of greater than about 20,000 $s^{-1}$. In some embodiments, the minimum clearance is in the range of from 0.5 mm to 2.5 mm.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a more detailed description of the preferred embodiment of the present invention, reference will now be made to the accompanying drawings, wherein.

NOTATION AND NOMENCLATURE

As used herein, the term "dispersion" refers to a liquefied mixture that contains at least two distinguishable substances (or "phases") that either will or will not readily mix and dissolve together. As used herein, a "dispersion" comprises a "continuous" phase (or "matrix"), which holds therein discontinuous droplets, bubbles, and/or particles of the other phase or substance. The term dispersion may thus refer to foams comprising gas bubbles suspended in a liquid continuous phase, emulsions in which droplets of a first liquid are dispersed throughout a continuous phase comprising a second liquid with which the first liquid is miscible or immiscible, and continuous liquid phases throughout which solid particles are distributed. As used herein, the term "dispersion" encompasses continuous liquid phases throughout in which gas bubbles are distributed, continuous liquid phases throughout in which solid particles are distributed, continuous phases of a first liquid throughout in which droplets of a second liquid that is soluble or insoluble in the continuous phase are distributed, and liquid phases throughout in which any one or a combination of solid particles, miscible/immiscible liquid droplets, and gas bubbles are distributed. Hence, a dispersion can exist as a homogeneous mixture in some cases (e.g., liquid/liquid phase), or as a heterogeneous mixture (e.g., gas/liquid, solid/liquid, liquid 1/liquid 2 or gas/solid/liquid), depending on the nature of the materials selected for combination. In the strictest sense, the properties of a homogeneous phase (e.g., density, viscosity) are continuous throughout the phase. A liquid/liquid mixture may be a heterogeneous mixture, e.g., oil and water, with one phase dispersed as bubbles throughout the other phase. Such a mixture is homogeneous macroscopically, though at the microscopic level it is heterogeneous. Therefore, homogeneous is used herein in the macroscopic sense unless otherwise specified.

Certain terms are used throughout the following description and claims to refer to particular system components. This document does not intend to distinguish between components that differ in name but not function.

In the following description and in the claims, the terms "including" and "comprising" are used in an open-ended fashion, and thus should be interpreted to mean "including, but not limited to . . . ".

DETAILED DESCRIPTION

Overview

A system and method employs an external high shear mechanical device to provide rapid contact and mixing of chemical ingredients in a controlled environment in the reactor/mixer device. The high shear device reduces the mass transfer limitations on the reaction and thus increases the overall reaction rate.

Chemical reactions involving liquids, gases and solids rely on the laws of kinetics that involve time, temperature, and pressure to define the rate of reactions. In cases where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there may be the additional rate limiting factor of having the reaction products removed from the surface of the catalyst to enable the catalyst to catalyze further reactants.

In conventional reactors, contact time for the reactants and/or catalyst is often controlled by mixing which provides contact between two or more reactants involved in a chemical reaction. A reactor assembly that comprises an external high shear mixer makes possible decreased mass transfer limitations and thereby allows the reaction to more closely approach kinetic limitations. When reaction rates are accelerated, residence times may be decreased, thereby increasing obtainable throughput. Alternatively, where the current yield is acceptable, decreasing the required residence time allows for the use of lower temperatures and/or pressures than conventional processes.

Shear Device Overview

High Shear devices (HSD) such as a high shear mixer, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 μm.

Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and can yield average particle size range from about 0.01 μm to about 1 μm. At the other end of the spectrum are high shear mixer systems classified as low energy devices. These systems usually have paddles or fluid rotors that turn at high speed in a reservoir of fluid to be processed, which in many of the more common applications is a food product. These systems are usually used when average particle, globule or bubble, sizes of greater than 20 microns are acceptable in the processed fluid.

Between low energy—high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, can achieve average particle, or bubble, sizes of about 0.01 μm to about 25 μm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

High Shear Device

Figure 1A:
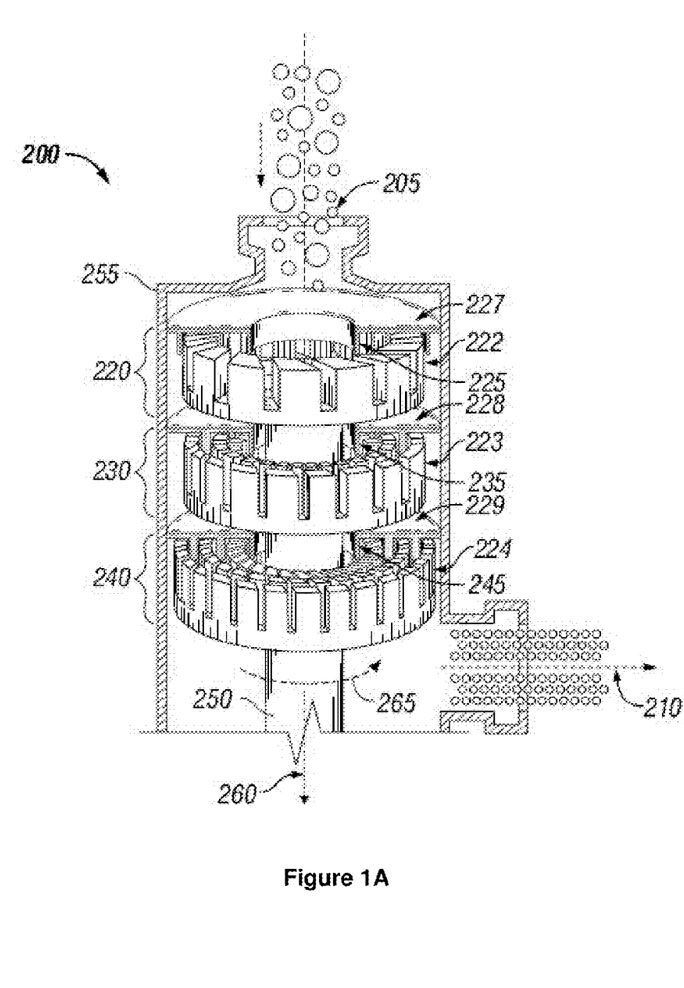
FIG. 1A is a longitudinal cross-section view of a three-stage shear device.
Figure 1B:
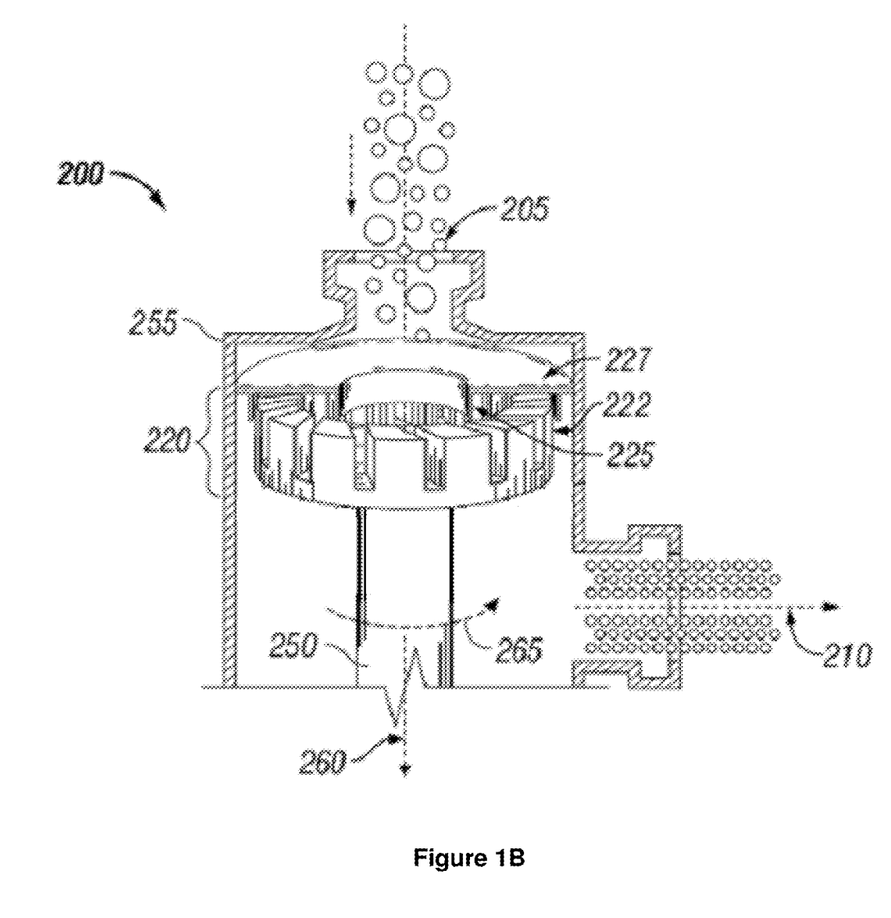
FIG. 1B is a longitudinal cross-section view of a one-stage shear device.

Referring now to FIG. 1A, there is presented a schematic diagram of a high shear device 200 with three rotor-stator combinations. The rotor-stator combinations may also be known as generators 220, 230, 240 or stages without limitation. Alternatively, the high shear device 200 comprises one generator as shown in FIG. 1B. In some other cases, the high shear device comprises two generators. As is readily seen, such high shear devices are constructed with one or more rotor-stator combinations according to the degree of mixing needed for each specific process.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. In embodiments, the inner diameter of the rotor is about 11.8 cm. In embodiments, the outer diameter of the stator is about 15.4 cm. In further embodiments, the rotor and stator may have an outer diameter of about 60 mm for the rotor, and about 64 mm for the stator. Alternatively, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 μm; preferably the bubbles are sub-micron in diameter. In certain instances, the average bubble size is in the range from about 1.0 μm to about 0.1 μm. Alternatively, the average bubble size is less than about 400 nm (0.4 μm) and most preferably less than about 100 nm (0.1 μm).

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation $V$ (m/sec) $=\pi \cdot D \cdot n$, where V is the tip speed, D is the diameter of the rotor, in meters, and n is the rotational speed of the rotor, in revolutions per second. Tip speed is thus a function of the rotor diameter and the rotation rate. Also, tip speed may be calculated by multiplying the circumferential distance transcribed by the rotor tip, $2\pi R$, where R is the radius of the rotor (meters, for example) times the frequency of revolution (for example revolutions (meters, for example) times the frequency of revolution (for example revolutions per minute, rpm).

For colloid mills, typical tip speeds are in excess of 23 m/sec (4500 ft/min) and can exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear mixer are produced during operation. In certain embodiments, the local pressure is at least about 1034 MPa (about 150,000 psi). The local pressure further depends on the tip speed, fluid viscosity, and the rotor-stator gap during operation.

An approximation of energy input into the fluid (kW/L/min) can be made by measuring the motor energy (kW) and fluid output (L/min). In embodiments, the energy expenditure of a high shear device is greater than 1000 W/m$^3$. In embodiments, the energy expenditure is in the range of from about 3000 W/m$^3$ to about 7500 W/m$^3$. The high shear device 200 combines high tip speeds with a very small shear gap to produce significant shear on the material. The amount of shear is typically dependent on the viscosity of the fluid. The shear rate generated in a high shear device 200 may be greater than 20,000 s$^{-1}$. In embodiments, the shear rate generated is in the range of from 20,000 s$^{-1}$ to 100,000 s$^{-1}$.

The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 μm in diameter may comprise a micro-foam. Not to be limited by a specific theory, it is known in emulsion chemistry that sub-micron particles, or bubbles, dispersed in a liquid undergo movement primarily through Brownian motion effects. Bubbles generated in the high shear process may have greater mobility and contact surface with the continuous phase and/or catalyst surfaces, thereby facilitating and accelerating the reaction through enhanced transport of reactants.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor. The accelerated rate reactor comprises a single stage dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a DISPAX® Reactor of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2HP power, output speed of 7900 rpm, flow capacity (water) approximately 300 l/h to approximately 700 l/h (depending on generator), a tip speed of from 9.4 m/s to about 41 m/s (about 1850 ft/min to about 8070 ft/min). Several alternative models are available having various inlet/outlet connections, horsepower, nominal tip speeds, output rpm, and nominal flow rate.

Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). The high shear mixing device of certain embodiments of the present system and methods is operated under what are believed to be cavitation conditions effective to promote cyclohexane oxidation.

High Shear Catalytic Oxidation

Figure 2A:
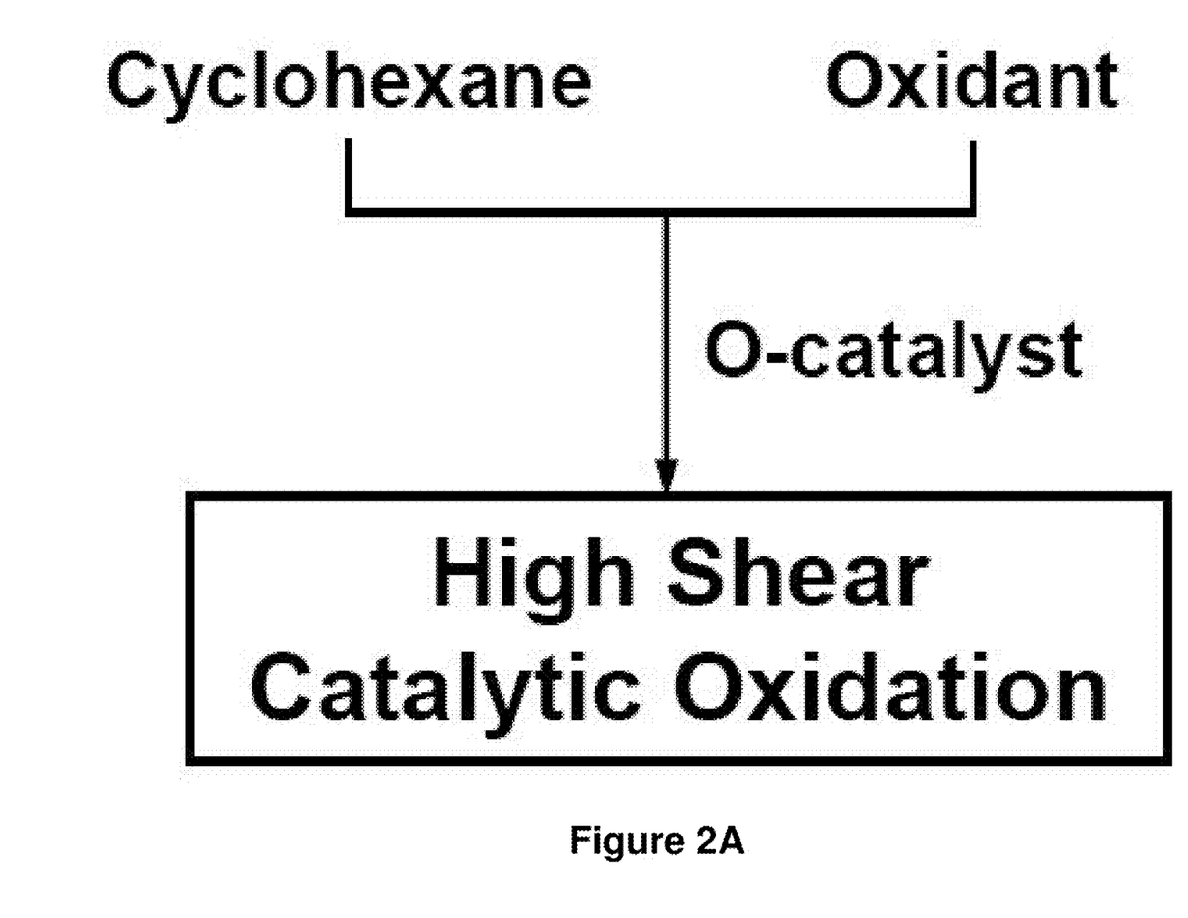
FIG. 2A schematically illustrates a high shear cyclohexane oxidation process, in accordance with an embodiment of the invention.

In an embodiment, as illustrated by FIG. 2A, a catalytic oxidation process of cyclohexane takes place under the application of high shear. Cyclohexane and an oxidant react under the catalytic action of an oxidation catalyst (O-catalyst) to produce products, such as cyclohexanol and cyclohexanone. The oxidant comprises air, oxygen-enriched air, oxygen, an oxygen-containing gas, ozone, peroxide, or organic peroxide. In some embodiments, the oxidation catalyst (O-catalyst) comprises the oxides of vanadium (V), manganese (Mn), nickel (Ni), copper (Cu), zinc (Zn), molybdenum (Mo), zirconium (Zr), or Cerium (Ce) over α-alumina support. In some other embodiments, cyclohexane oxidation catalysts comprise soluble transition metal compounds, such as a cobalt ester of naphthenic acid, octanoic acid, 2-ethylhexanoic acid, or other carboxylic acids. In other embodiments the oxidation is catalyzed in the presence of a noble metal catalyst.

Figure 2B:
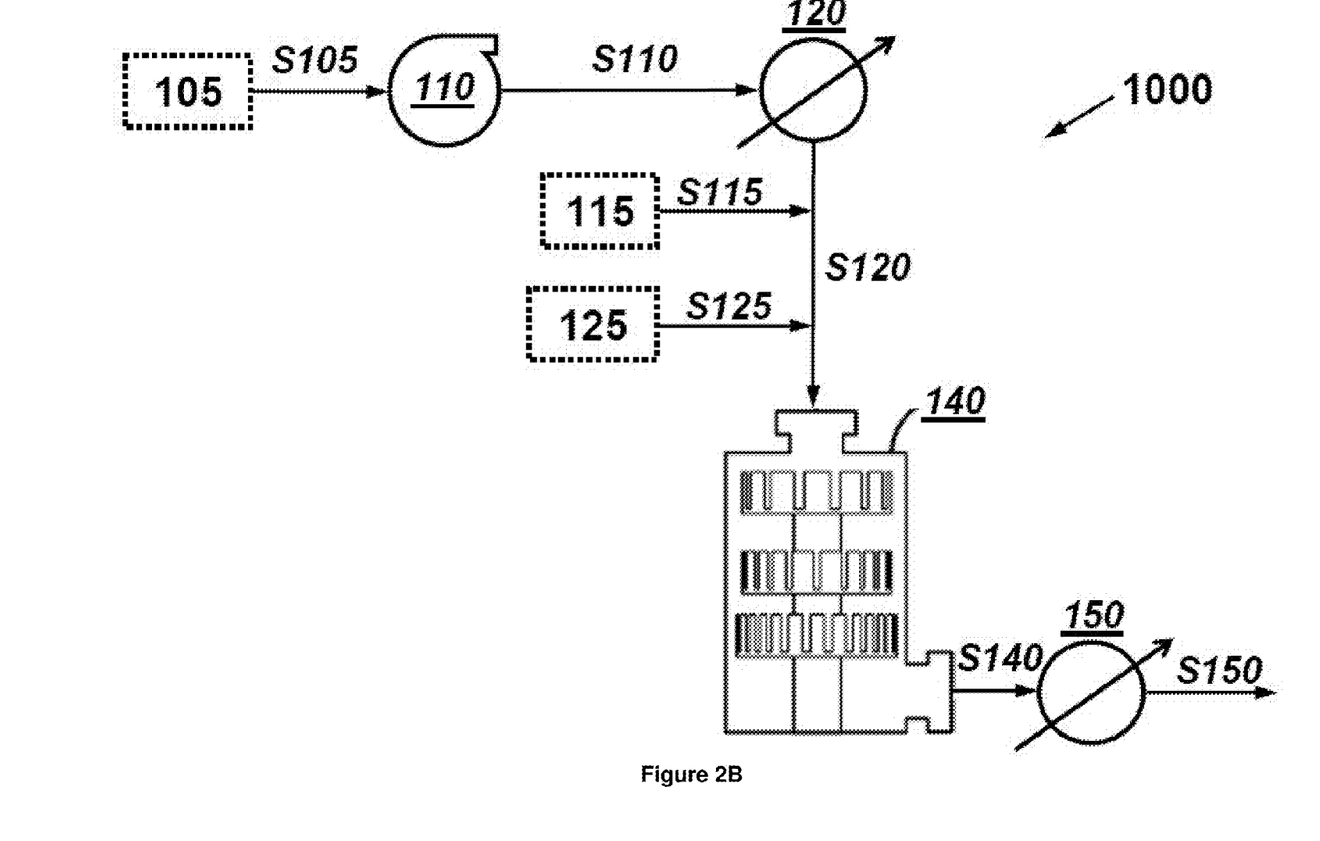
FIG. 2B schematically illustrates a high shear cyclohexane oxidation system, in accordance with an embodiment of the invention.

In an embodiment, as shown by FIG. 2B, a cyclohexane catalytic oxidation system 1000 comprises pump 110, heat exchangers 120 and 150, and shear device 140. System 1000 also comprises cyclohexane source 105, oxidant source 115, and O-catalyst source 125.

Cyclohexane is sent from cyclohexane source 105 to pump 110 as stream S105, exits as stream S110, passes through heat exchanger 120, and exits as stream S120. An oxidant source 115 sends stream S115 to be mixed with stream S120. In some cases, the oxidant comprises an oxygen-containing gas, such as air, oxygen, oxygen-enriched air. In some embodiments, O-catalyst source 125 sends stream S125 to be mixed with stream S120.

Stream S120, after being mixed with streams S115 and S125, is sent to shear device 140, where catalytic oxidation of cyclohexane takes place. Stream S140 exits shear device 140 and enters heat exchanger 150 to be cooled, and exits as stream S150. In some embodiments, stream S150 is further processed. In some cases, stream S150 passes through a flash system to rid of any unwanted volatile components. In some other cases, stream S150 is recycled (not shown in FIG. 2B) for further oxidation.

For applications in which solid particles are to be sent through high shear device 140, the appropriate shear gap width (minimum clearance between rotor and stator) may be selected for an appropriate reduction in particle size and increase in particle surface area. In embodiments, this may be beneficial for increasing catalyst surface area by shearing and dispersing the particles.

The performance of the high shear cyclohexane oxidation system (e.g., the rate and selectivity of production of cyclohexanol and cyclohexanone) depends on parameters including residence time, reaction temperature, oxidant concentration, and catalyst concentration. Not to be limited by theory, it is known in emulsion chemistry that sub-micron particles, or bubbles, dispersed in a liquid undergo movement primarily through Brownian motion effects. The bubbles in the product dispersion created by high shear device 140 may have greater mobility through boundary layers of solid catalyst particles, thereby facilitating and accelerating the catalytic reaction through enhanced transport of reactants. Therefore, the improved hydrodynamics provided by the high shear device allows the catalytic reaction to be operated at either lower temperature or shorter residence time or a combination of both, whereby reducing the extent of undesired reactions.

In some embodiments, the catalytic oxidation of cyclohexane takes place in the high shear device 140 at a temperature in the range of from 60° C. to 200° C., alternatively from 80° C. to 180° C., alternatively from 100° C. to 160° C. In some embodiments, the catalytic oxidation of cyclohexane takes place in the high shear device 140 at a pressure in the range of from 0.1 MPa to 5 MPa, alternatively from 0.3 MPa to 3 MPa, alternatively from 0.5 MPa to 2.5 MPa. Catalyst concentration is dependent on the type catalyst used and operating conditions. Catalyst concentration would typically be in the parts per million level (e.g., 1 ppm to 100 ppm based on metal content). In some embodiments the catalyst is enclosed in a fixed bed reactor located at the outlet of the high shear device.

In some embodiments, O-catalyst source 125 is omitted and high shear device 140 comprises at least one catalytic surface in any of the rotor/stator stages. The catalytic surface contains an oxidation catalyst. In some cases, the catalytic surface is constructed to be part of a rotor. In some cases, the catalytic surface is constructed to be part of a stator. In some cases, the catalytic surface is constructed to be part of a rotor and a stator. When cyclohexane and the oxidant are introduced into shear device 140, a catalytic oxidation reaction is induced when the mixture comes in touch with the catalytic surface.

In some embodiments, if a large portion of gaseous products or reactants are in the effluent stream S140 of shear device 140, the inlet of a vessel configured for gas vent may be connected to stream S140 (not shown in FIG. 2B). The volatile components are taken out of the system to ensure safe and efficient operation. Furthermore, an inert gas (e.g., nitrogen) may be used in such a gas vent vessel to strip dissolved gaseous components from the mixture. This stripping step removes residual oxidant (e.g., oxygen) from the effluent mixture of oxygenated products. In some cases, dissolved oxygen is rapidly removed, thus minimizing further reactions.

High Shear Oxidation-Hydrogenation

Figure 3A:
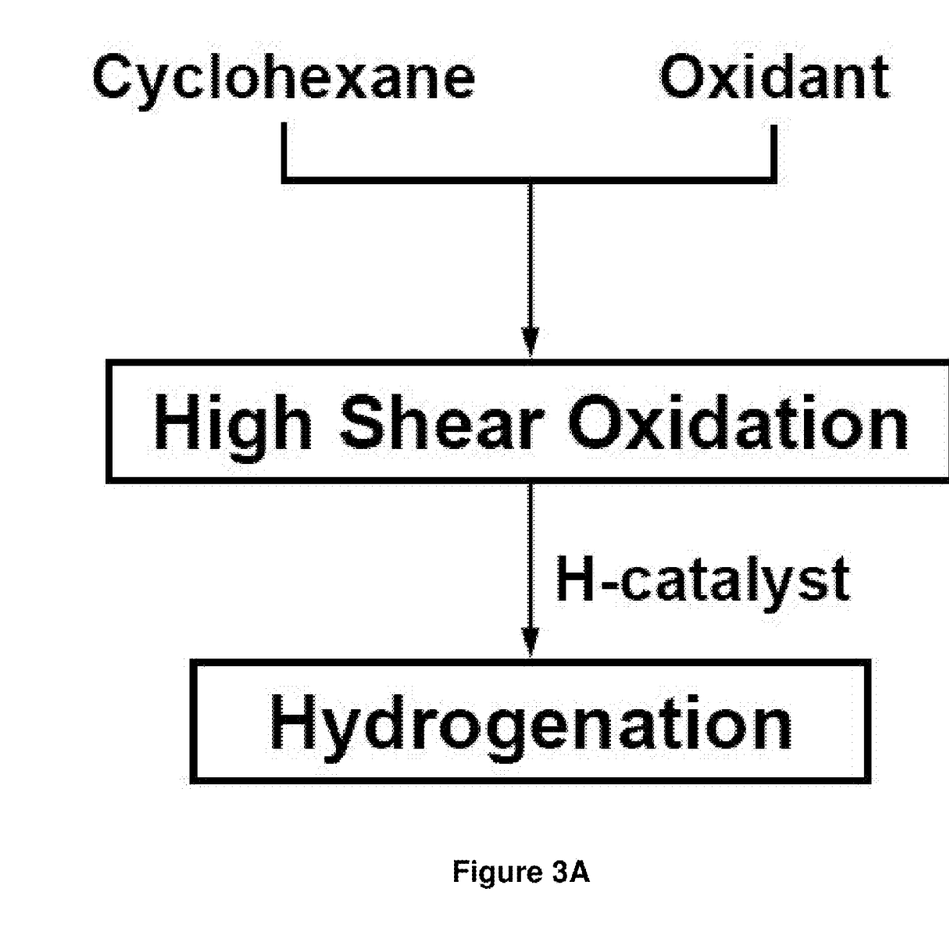
FIG. 3A schematically illustrates a high shear cyclohexane oxidation-hydrogenation process, in accordance with an embodiment of the invention.

In another embodiment, as illustrated by FIG. 3A, an oxidation-hydrogenation process of cyclohexane takes place under the application of high shear. In this case, the use of oxidation catalyst (O-catalyst) is omitted. Cyclohexane is oxidized under the application of high shear and a series of cyclohexanol and cyclohexanone precursors are produced. These precursors are then catalytically hydrogenated to produce cyclohexanol and cyclohexanone. These precursors comprise, but are not limited to, one or more of cyclohexyl hydroperoxide, ketals, acetals, 1,1' oxybiscyclohexane, cyclohexyl esters of monocarboxylic and dicarboxylic acids, 7-oxabicycloheptane, 2-hydroxycyclohexanone, 2h-pyran-2-one tetrahydro, 2-oxepanone. Among these precursors, cyclohexyl hydroperoxide is one of the most abundant.

The hydrogenation catalyst (H-catalyst) may take the form of a heterogeneous fixed bed catalyst, a slurry phase catalyst or a homogeneous catalyst. The catalyst may be any one of the conventional hydrogenation catalysts such as the noble metals. The noble metal is normally supported on an inert carrier such as palladium on a high surface area carbon support. In some embodiments, a nickel hydrogenation catalyst is utilized.

Figure 3B:
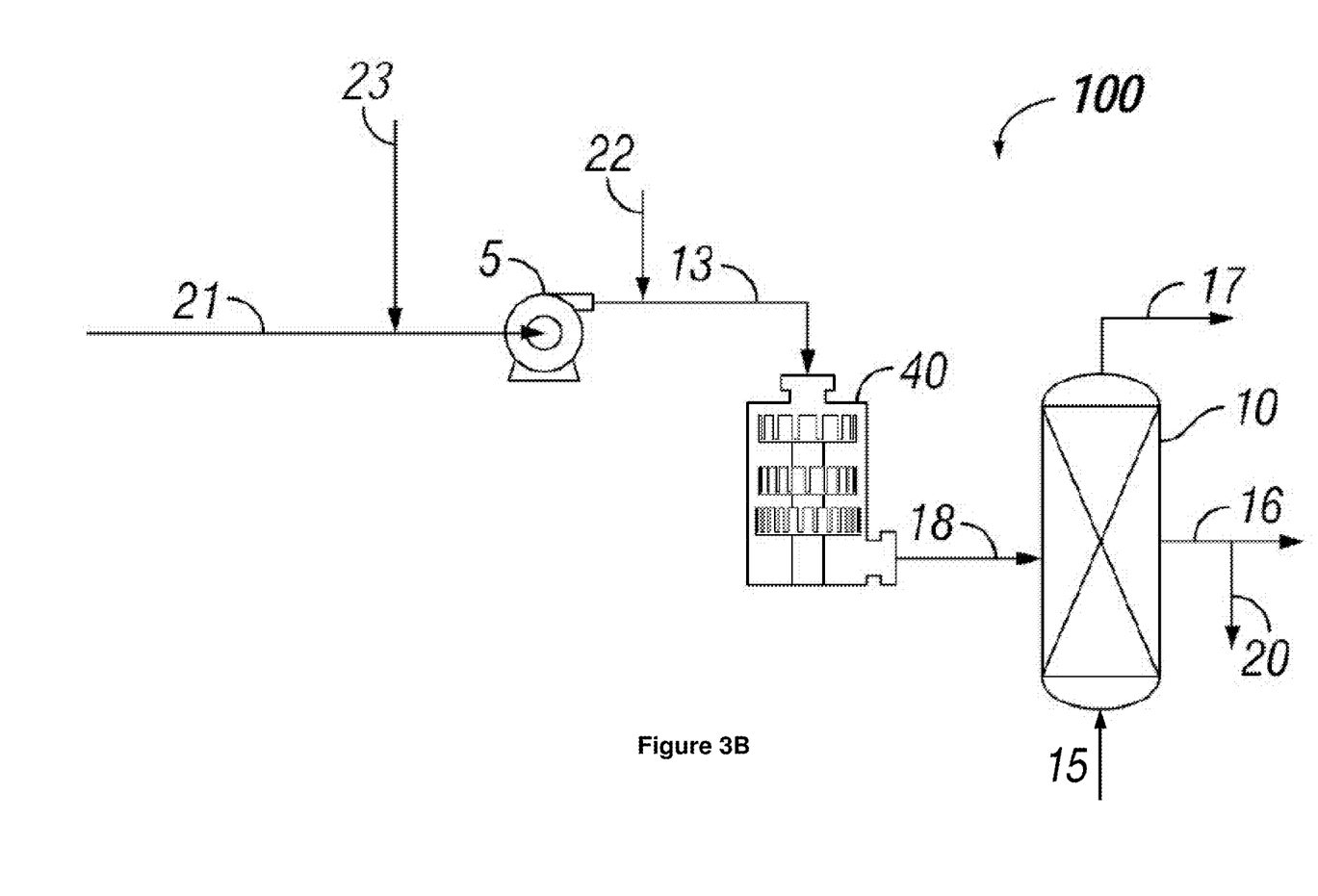
FIG. 3B schematically illustrates a high shear cyclohexane oxidation-hydrogenation system, in accordance with an embodiment of the invention.

In a further embodiment, as shown by FIG. 3B, a high shear oxidation-hydrogenation system 100 for cyclohexane is presented. System 100 comprises pump 5, high shear mixing device (HSD) 40, and hydrogenation reactor 10. As shown in FIG. 3B, high shear device 40 is located external to hydrogenation reactor 10. Each of these components is further described in more detail below. Stream 21 represents the cyclohexane feed stream, which is connected to pump 5 to be introduced into HSD 40. One of both of stream 23 and stream 22 may be used for oxidant introduction. The oxidant is mixed with cyclohexane and sent to HSD 40 as stream 13.

Effluent stream 18 from HSD 40 is sent to hydrogenation reactor 10. Stream 15 introduces a hydrogen-containing gas (e.g., $H_2$) into reactor 10. Effluent stream 17 from reactor 10 removes unreacted hydrogen and/or other reaction or product gases. Hydrogenated products (e.g., cyclohexanol and cyclohexanone) are extracted via stream 16. In some embodiments, a portion or all of the extracted products is recycled via stream 20 for multi-pass processing. Additional components or process steps may be incorporated throughout system 100, if desired, as will become apparent upon reading the description of the process described hereinbelow. For example, stream 20 may be connected to stream 21 or stream 13, to provide for recirculation through HSD 40 and reactor 10 (not shown in FIG. 3B).

In some embodiments, if a large portion of gaseous products or reactants are in the effluent stream 18 of HSD 40, the inlet of a vessel configured for gas vent may be connected to stream 18 (not shown in FIG. 3B). These volatile components are taken out of the system to ensure safe and efficient operation. Furthermore, an inert gas (e.g., nitrogen) may be used in such a gas vent vessel to strip the mixture before the hydrogenation step. This stripping step removes residual oxidant (e.g., oxygen) from the effluent mixture of oxygenated products. In some cases, dissolved oxygen is rapidly removed, thus minimizing further decomposition reactions. In addition, any dissolved carbon monoxide, a known hydrogenation catalyst poison, is removed, thereby improving catalyst life.

Reactor. Hydrogenation reactor 10 (FIG. 3B) is any type of vessel in which hydrogenation can propagate. For instance, a continuous or semi-continuous stirred tank reactor, or one or more batch reactors may be employed in series or in parallel. In some applications reactor 10 may be a tower reactor, and in others a tubular reactor or multi-tubular reactor. Any number of reactor inlet lines is envisioned, with two shown in FIG. 3B (streams 18 and 15). An inlet line (not shown in FIG. 3B) may be used to introduce a catalyst or catalyst slurry to reactor 10 in certain embodiments. Reactor 10 may comprise an exit stream 17 for vent gas, and an outlet product stream 16 for a hydrogenated product stream. In embodiments, reactor 10 comprises a plurality of reactor product streams (e.g., stream 16).

When reactor 10 is utilized, reactor 10 may be operated as a slurry reactor, a fixed bed reactor, a trickle bed reactor, a fluidized bed reactor, a bubble column, or other method known to one of skill in the art. Reactor 10 may be the primary location for the hydrogenation reaction to occur due to the presence of catalyst and its effect on the rate of hydrogenation. Thus, reactor 10 may be any type of reactor(s) in which hydrogenation may propagate. For example, reactor 10 may comprise one or more tanks or tubular reactors in series or in parallel. The hydrogenation reaction may be a homogeneous catalytic reaction in which the catalyst is in the same phase as another component of the reaction mixture or a heterogeneous catalytic reaction involving a solid catalyst.

Reactor 10 may include one or more of the following components: stirring system, heating and/or cooling capabilities, pressure measurement instrumentation, temperature measurement instrumentation, one or more injection points, and level regulator (not shown), as are known in the art of reaction vessel design. For example, a stirring system may include a motor driven mixer. A heating and/or cooling apparatus may comprise, for example, a heat exchanger.

Hydrogenation reactor 10 may be operated in either continuous or semi-continuous flow mode, or it may be operated in batch mode. The contents of reactor 10 may be maintained at a specified reaction temperature using heating and/or cooling capabilities (e.g., cooling coils) and temperature measurement instrumentation. Pressure in the vessel may be monitored using suitable pressure measurement instrumentation, and the level of reactants in the vessel may be controlled using a level regulator (not shown), employing techniques that are known to those of skill in the art. The contents may be stirred continuously or semi-continuously.

Heat Transfer Devices. In addition to the above-mentioned heating/cooling capabilities of reactor 10, other external or internal heat transfer devices for heating or cooling a process stream are also contemplated in variations of the embodiments illustrated in FIG. 3B. For example, heat may be added to or removed from reactor 10 via any method known to one skilled in the art. The use of external heating and/or cooling heat transfer devices is also contemplated. Some suitable locations for one or more such heat transfer devices are between pump 5 and HSD 40, between HSD 40 and reactor 10, and between reactor 10 and pump 5 when oxidation-hydrogenation is operated in multi-pass mode. Some non-limiting examples of such heat transfer devices are shell, tube, plate, and coil heat exchangers, as are known in the art.

Pumps. Pump 5 is configured for either continuous or semi-continuous operation, and may be any suitable pumping device that is capable of providing greater than 202.65 kPa (2 atm) pressure, preferably greater than 303.975 kPa (3 atm) pressure, to allow controlled flow through HSD 40. For example, a Roper Type 1 gear pump, Roper Pump Company (Commerce Georgia) Dayton Pressure Booster Pump Model 2P372E, Dayton Electric Co (Niles, Ill.) is one suitable pump. Preferably, all contact parts of the pump comprise stainless steel, for example, 316 stainless steel. In some embodiments of the system, pump 5 is capable of pressures greater than about 2026.5 kPa (20 atm). In addition to pump 5, one or more additional, high pressure pump(s) (not shown) may be included in the systems illustrated in FIG. 3B. For example, a booster pump, which may be similar to pump 5, may be included between HSD 40 and reactor 10 for boosting the pressure into reactor 10, or a recycle pump may be positioned on stream 17 for recycling gas from reactor 10 to HSD 40. As another example, a supplemental feed pump, which may be similar to pump 5, may be included.

In some embodiments, the catalytic oxidation of cyclohexane takes place in the high shear device 140 at a temperature in the range of from 60° C. to 200° C., alternatively from 80° C. to 180° C., alternatively from 100° C. to 160° C. In some embodiments, the catalytic oxidation of cyclohexane takes place in the high shear device 140 at a pressure in the range of from 0.1 MPa to 5 MPa, alternatively from 0.3 MPa to 3 MPa, alternatively from 0.5 MPa to 2.5 MPa. Catalyst concentration is dependent on the type catalyst used and operating conditions. Catalyst concentration would typically be in the parts per million level (e.g., 1 ppm to 100 ppm based on metal content).

In some embodiments, the temperature in hydrogenation reactor 10 is in the range of from 100° C. to 300° C., alternatively from 125° C. to 250° C., alternatively from 150° C. to 200° C. In some embodiments, the pressure in hydrogenation reactor 10 is in the range of from 0.1 MPa to 10 MPa, alternatively from 1 MPa to 8 MPa, alternatively from 2 MPa to 5 MPa. The feed weight hourly space velocity (WHSV), which is herein understood to mean the unit weight of feed per hour entering the reactor per unit weight of catalyst in the catalytic structure, may vary over a wide range within the other operation condition perimeters, e.g., from 0.1 to 35. In some embodiments, hydrogenation takes place in a fixed bed reactor containing nickel or noble metal catalyst.

High Shear Catalytic Oxidation-hydrogenation

Figure 4:
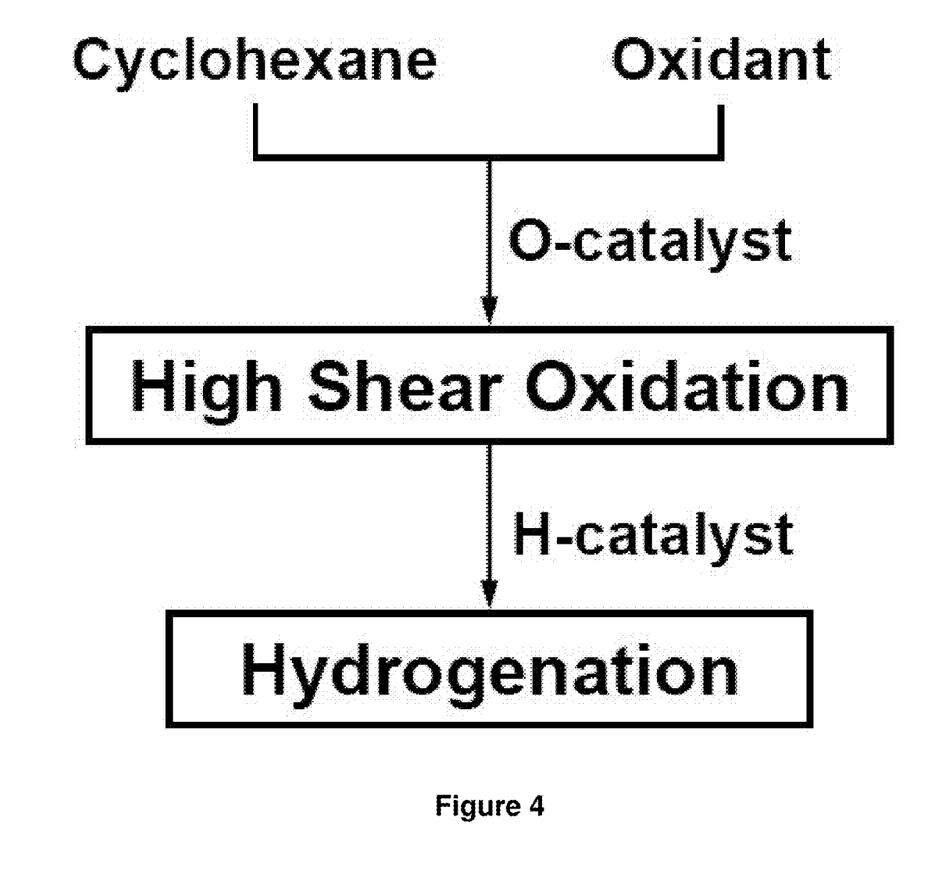
FIG. 4 schematically illustrates a high shear catalytic cyclohexane oxidation-hydrogenation process, in accordance with another embodiment of the invention.

In yet a further embodiment, as illustrated by FIG. 4, a catalytic oxidation-hydrogenation process of cyclohexane takes place under the application of high shear. In this case, both oxidation catalyst (O-catalyst) and hydrogenation (H-catalyst) are utilized. Cyclohexane is oxidized under the application of high shear and an O-catalyst. Cyclohexanol and cyclohexanone and a series of cyclohexanol and cyclohexanone precursors are produced. The product mixture is then hydrogenated under the action of a H-catalyst. The precursors are converted to produce additional cyclohexanol and cyclohexanone. With the aid of the disclosure provided herein, one of ordinary skill in the art will be able to conceive many configurations to carry out the high shear catalytic oxidation-hydrogenation process for cyclohexane. Therefore, all these configurations are within the scope of the invention.

In various embodiments, the dispersion that enters the hydrogenation stage is substantially free of oxygen. In some cases, an oxidation reactor is coupled to a high shear device and configured to receive the dispersion from the high shear device and allow oxidation reactions to complete so that the oxygen in the dispersion is substantially consumed. In some embodiments, the oxidation reactor comprises a fixed-bed catalyst. In other embodiments, the oxidation reactor may be operated as a slurry reactor, a fixed bed reactor, a trickle bed reactor, a fluidized bed reactor, a bubble column, or other method known to one of skill in the art. Such a reactor may be the primary location for the oxidation reaction to occur due to the presence of catalyst and its effect on the rate of oxidation. Thus, the oxidation reactor may be any type of reactor(s) in which oxidation may propagate. For example, the oxidation reactor may comprise one or more tanks or tubular reactors in series or in parallel. The oxidation reaction may be a homogeneous catalytic reaction in which the catalyst is in the same phase as another component of the reaction mixture or a heterogeneous catalytic reaction involving a solid catalyst. In some embodiments, multiple oxidation reactors are coupled to the high shear device to allow oxidation reactions to develop and complete. In some embodiments, multiple high shear devices (in series or in parallel or combined in-series and in-parallel configuration) are utilized for the oxidation stage of cyclohexane oxidation. In some other cases, multiple high shear devices coupled with multiple oxidation reactors (in series or in parallel or combined in-series and in-parallel configuration) are utilized for the oxidation stage of cyclohexane oxidation.

In some embodiments, a high shear device is utilized in the hydrogenation stage for cyclohexane oxidation. After the dispersion exits the oxidation stage, it is subjected under high shear to mix with hydrogen. In some cases, the dispersion mixed with the hydrogen is introduced into a hydrogenation reactor containing a hydrogenation catalyst for hydrogenation reactions to develop. In some other cases, the dispersion is mixed with a hydrogenation catalyst slurry and hydrogen in a shear device and then sent to a reactor for hydrogenation reactions to develop. The hydrogenation reactions may take place in both the shear device and the reactor. In some further cases, the dispersion is mixed with hydrogen in a shear device having a catalytic surface that promotes hydrogenation reactions.

High Shear Air Oxidation of Cyclohexane

Figure 5:
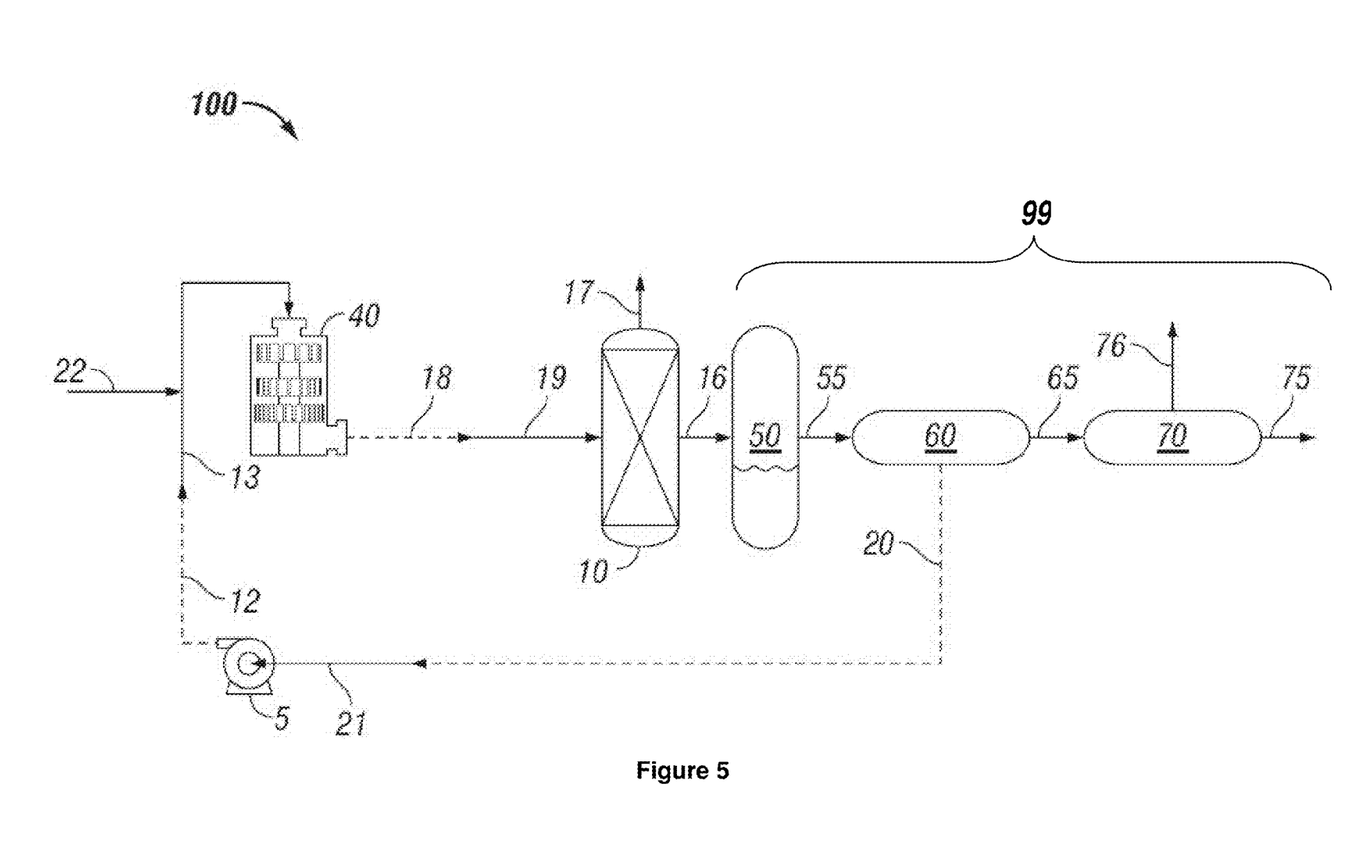
FIG. 5 is a process flow diagram of a system for the air oxidation of cyclohexane, according to an embodiment of the invention.

FIG. 5 is a schematic of a flow diagram of a cyclohexane air oxidation process employing a multi-phase reaction system and comprising an external high shear mixer. High Shear System 100, hereinafter HSS 100, is suitable for the air oxidation of cyclohexane. As will be further discussed below, the disclosed mediator high shear process reduces resistance to mass and heat transfer between multiple phases during the oxidation reaction. Furthermore, as discussed below, air oxidation in the absence of an oxidation catalyst will be described, although it may be understood by one skilled in the art a catalyst may further be implemented to improve reaction conditions.

FIG. 5 illustrates the basic components of a representative high shear system 100 comprising pump 5, high shear device 40, and reactor 10. High shear device 40 is positioned between pump 5 and reactor 10. Pump 5 is used to provide a controlled flow throughout high shear device (HSD) 40 and high shear system 100 for cyclohexane oxidation. Pump inlet stream 21 comprises liquid cyclohexane for introduction to pump 5. Pump 5 increases the pressure of the pump inlet stream 21 to greater than about 203 kPa (about 2 atm); alternatively, the inlet stream 21 is pressurized to greater than about 304 kPa (about 3 atm). Additionally, pump 5 may build pressure throughout HSS 100. In this way, HSS 100 combines high shear with pressure to enhance reactant intimate mixing. Preferably, all contact parts of pump 5 are stainless steel, for example, 316 stainless steel. Pump 5 may be any suitable pump, for example, a Dayton Pressure Booster Pump Model 2P372E, Dayton Electric Co (Niles, Ill.).

The pressurized, liquid cyclohexane exits pump 5 via pump exit stream 12. Pump exit stream 12 is in fluid communication with HSD inlet stream 13. Further, HSD inlet stream 13 is in fluid communication with the HSD 40. In certain instances, dispersible gas stream 22 comprising an oxidant gas is introduced or injected to HSD inlet stream 13. In certain embodiments, the oxidant gas in dispersible gas stream 22 comprises air. Alternatively, the oxidant gas may be any gas known to one skilled in the art for oxidizing cyclohexane to cyclohexanol. In some embodiments the oxidant gas in dispersible gas stream 22 may continuously be fed into exit stream 12 to form HSD inlet stream 13. HSD inlet stream 13 comprises a mixture of oxidant gas and liquid cyclohexane. Dispersible gas stream 22 and pressurized pump exit stream 12 may be injected separately into HSD inlet stream 13 for processing by high shear device 40. In certain instances, HSD inlet stream 13 may undergo further processing or treating steps prior to introduction into HSD 40.

HSD 40 in fluid communication with HSD inlet stream 13. Alternatively, multiple high shear devices 40 are in fluid communication with HSD inlet stream 13. HSD 40 serves to intimately mix the cyclohexane solution in pump exit stream 12 with dispersible gas stream 22. As discussed in detail above, high shear device 40 is a mechanical device that utilizes, for example, a stator rotor mixing head with a fixed gap between the stator and rotor. In high shear device 40, the oxidant gas and cyclohexane are mixed to form an emulsion comprising microbubbles and nanobubbles of the oxidant gas. In embodiments, the resultant dispersion comprises bubbles in the submicron size. In embodiments, the resultant dispersion has an average bubble size less than about 1.5 μm. In embodiments, the mean bubble size is less than from about 0.1 μm to about 1.5 μm. Not to be limited by a specific method, it is known in emulsion chemistry that submicron particles dispersed in a liquid undergo movement primarily through Brownian motion effects. Thus it is believed that submicron gas particles created by the high shear device 40 have greater mobility through boundary layers of solid catalyst particles thereby facilitating and accelerating the catalytic reaction through greater transport of reactants. In embodiments, the high shear mixing produces gas bubbles capable of remaining dispersed at atmospheric pressure for about 15 minutes or longer depending on the bubble size. In embodiments, the mean bubble size is less than about 400 nm; more preferably, less than about 100 nm. HSD 40 serves to create an emulsion of oxidant gas bubbles within high shear inlet stream 13 comprising cyclohexane and air. The emulsion may further comprise a micro-foam.

In certain embodiments, the formation of an air and cyclohexane emulsion initiates the air oxidation reactions that form cyclohexanol. Air oxidation reactions may occur whenever suitable time, temperature, and pressure conditions exist. In this sense air oxidation could occur at any point in the flow diagram of FIG. 5 if temperature and pressure conditions are suitable. In certain embodiments comprising a slurry based catalyst, reaction is more likely to occur at points outside reactor 10 shown in FIG. 5. In such embodiments, a discrete reactor is often desirable to allow for increased residence time, agitation and heating and/or cooling. In embodiments wherein a fixed bed catalyst is utilized, the presence of catalyst in the emulsion will affect the rate of air oxidation.

The emulsion exits HSD 40 via HSD exit stream 18. High shear device exit stream 18 fluidly couples HSD 40 and reactor 10. Further, the emulsion exits HSD 40 via HSD exit stream 18. HSD exit stream 18 is in fluid communication with reactor inlet stream 19. Reactor inlet stream 19 couples HSD inlet stream 18 and reactor 10. In certain embodiments, HSD exit stream 18, and reactor inlet stream 19 are analogous; and in further instances, HSD exit stream 18 comprises reactor inlet stream 19. Alternatively, reactor inlet stream 19 may comprise HSD exit stream 18 which optionally has undergone further processing prior to introduction to reactor 10.

In FIG. 5, the reactor 10 is any type of reactor in which the multiphase air oxidation reaction can propagate. The reactor 10 may be an oxidation tower reactor, a stirred tank rank, a static tank reactor, a stirred autoclave reactor, or a non-stirred autoclave reactor. Furthermore, reactor 10 may comprises a plurality of reactors, and in certain embodiments, reactor 10 may include a combination of different reactors. In certain embodiments, reactor 10 is configured as a semi-continuous, stirred, tank reactor.

Reactor 10 serves to contain the oxidant gas, e.g. air, and the cyclohexane for the oxidation reaction to produce cyclohexanol. In embodiments, the temperature for air oxidation of cyclohexane is less than about 160° C., and preferably the temperature for air oxidation of cyclohexane is from about 80° C. to about 150° C. Additionally, heat exchangers may be used to maintain the reaction temperature in the reactor. Suitable locations for external heat transfer devices would be between the reactor 10 and the pump 5; between the pump 5 and the high shear mixer 40 or between the high shear mixer 40 and the reactor 10. There are many types of heat transfer devices that may be suitable and are known to those experienced in the art. Such exchangers might include shell and tube, plate, and coil heat exchangers. In embodiments, reactor 10 may primarily serve to cool fluid, as much of the reaction occurs in external high shear mixer 40 and throughout HSS 100. Furthermore, reactor 10 may comprise gas vent 17 for removing excess oxidant gas comprising air from HSS 100.

Reactor 10 is emptied by product stream 16. Product stream 16 comprising cyclohexanol, cyclohexanone, unconverted cyclohexane, cyclohexyl-hydroperoxide (CHHP), and any other byproducts may be further processed to isolate cyclohexanol or cyclohexanone. Upon removal from reactor 10, product stream 16 comprising cyclohexanol may be passed to product recovery systems downstream of reactor 10 for further processing as known to those of skill in the art.

For example, product stream 16 may be in fluid communication with a ketone-alcohol (KA) distillation system 99. The KA oil distillation system comprises thermal treatment vessel 50 and a plurality of distillation columns 60, 70. In certain instances CHHP may be decomposed to produce additional cyclohexanone (ketone, K) and cyclohexanol (alcohol, A) by KA distillation system 99.

In embodiments, decomposition vessel 50 is configured for the decomposition of CHHP. The product stream 55 from decomposition vessel 50 is in fluid communication with at least distillation column 60. In certain embodiments, there is a plurality of distillation columns 60. Distillation column(s) 60 are configured to separate unreacted cyclohexane stream 20 for recycling to pump inlet stream 21. Distillation column(s) 60 produce distillate stream 65, comprising cyclohexanol, and/or cyclohexanone. In certain embodiments, distillate stream 65 comprises crude ketone-alcohol (KA). Furthermore distillate 65 from distillation column(s) 60 is fluidly coupled to second distillation column(s) 70. Second distillation column(s) 70 further refine distillate 65 to produce refined KA stream 76 and non volatile tails stream 75.

In KA oil distillation system 99, product stream 16 undergoes thermal decomposition of CHHP 50 to produce more of desirable products as described herein, in the decomposition vessel 50. Decomposition of CHHP may be performed, for example, via thermal decomposition, catalytic decomposition, catalytic hydrogenation, or other catalytic methods, such as the use of gold catalyst and the like. Thermal decomposition may be performed at temperatures of from about 120° C. to about 175° C. CHHP hydrogenation is carried out with heterogeneous catalysts, at temperatures between about 100° C. to about 160° C. Hydrogenation catalysts include but not limited to palladium on silica or alumina support. In embodiments, CHHP decomposition is accomplished without hydrogen via the use of different heterogeneous catalysts such as gold deposited on silica or alumina at temperatures between about 100° C. and about 160° C. In embodiments, CHHP decomposition is accomplished by metal catalyzed decomposition in caustic aqueous solution. This may be achieved by contacting the CHHP with cobalt, chromium, or a mixture thereof, in caustic solutions, preferably sodium hydroxide. When using either, or both, of these metals for CHHP decomposition the concentration of Co and/or Cr may be between 0.1 and 20 ppm. In embodiments, decomposition vessel 50 is configured to maintain a temperature of at least 100° C.

Product stream 55, from decomposition vessel 50, is in fluid communication with distillation column(s) 60. Distillation column(s) 60 are configured such that the unconverted or, unreacted cyclohexane stream 20 may be distilled off and, in embodiments, recycled to pump inlet stream 21. The resulting distillate 65 comprising crude KA may be further refined in second distillation column(s) 70. In embodiments, second distillation column(s) 70 is operated at temperatures between from about 90° C. to about 170° C. Refined KA is distilled from second distillation column(s) 70 as stream 76, while nonvolatile residue tails stream 75 is collected from the bottom of second distillation column(s) 70 for other processes. In alternative instances, cyclohexane distillation and KA refining may be performed by different unit operations known to those of skill in the art, such as vacuum distillation, steam distillation, and the like, without limitation.

In embodiments, use of the disclosed process comprising reactant mixing by high shear device 40 allows use of lower temperature and/or pressure in reactor 10 than previously enabled. In embodiments, the high shear process provides a higher conversion of cyclohexane to cyclohexanol/cyclohexanone and/or decreased volumes of vent gas stream 17 due to more efficient air oxidation. In embodiments, the method comprises incorporating high shear device 40 into an established process thereby reducing the operating temperature and/or pressure of the reaction in external high shear reactor 40 and/or enabling the increase in production (greater throughput) compared to a process operated without high shear device 40. The process of the present invention should be conducted under conditions sufficient to promote the air oxidation of cyclohexane in the reactive mixture. It will be understood by those skilled in the art that conditions of temperature and pressure may vary depending on other variables such as the desired conversion, cyclohexane concentration, the heating/cooling efficiency of the reactor system, etc.

In embodiments, the method and system of this disclosure enable design of a smaller and/or less capital intensive process allowing selection of a reactor 10 having lower operating temperature and/or pressure capability than previously possible without the incorporation of external high shear mixer 40. In embodiments, the disclosed method reduces operating costs/increases production from an existing process. Alternatively, the disclosed method may reduce capital costs for the design of new processes. Potential benefits of this modified system include, but are not limited to, faster cycle times, increased throughput, reduced operating costs and/or reduced capital expense due to the possibility of designing smaller reactors and/or operating the reactor at lower temperature and/or pressure.

In embodiments, the process of the present disclosure provides for a residence time less than about ¾ the residence time for air oxidation of cyclohexane in the absence of external high shear mixing. In embodiments, the process of the present disclosure provides for a residence time of less than about ½ the residence time (for the same conversion) when compared to air oxidation of cyclohexane in the absence of external high shear mixing.

Operation Modes

With the embodiments described above, it is easily conceivable to one skilled in the art that high shear oxidation of cyclohexane may be carried out continuously, semi-continuously, or batch-wise. Material processed through the high shear device may alternatively be recycled or sent through additional high shear devices for further oxidation. Therefore, operation modes of the presented high shear oxidation process are not to limit the scope of the invention but to be considered as equivalents of the invention.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations. of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The inclusion or discussion of a reference is not an admission that it is prior art to the present invention, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

What is claimed is:

1. A method comprising:
   a) forming a dispersion comprising liquid cyclohexane and an oxidant gas utilizing a high shear device, wherein the dispersion comprises oxidant gas bubbles with a mean diameter of less than about 5 µm, and wherein the high shear device comprises at least one rotor and at least one stator; and
   b) hydrogenating the dispersion in the presence of a hydrogenation catalyst to form a product comprising cyclohexanol or cyclohexanone.

2. The method of claim 1 wherein said oxidant gas comprises air, oxygen-enriched air, oxygen, or an oxygen-containing gas.

3. The method of claim 1 wherein step a) comprises forming said dispersion in the presence of an oxidation catalyst.

4. The method of claim 3 wherein said oxidation catalyst comprises the oxides of vanadium (V), manganese (Mn), nickel (Ni), copper (Cu), zinc (Zn), molybdenum (Mo), zirconium (Zr), or Cerium (Ce) over α-alumina support.

5. The method of claim 3 wherein said oxidation catalyst comprises a soluble transition metal compound.

6. The method of claim 5 wherein said soluble transition metal compound comprises a cobalt ester of naphthenic acid, octanoic acid, 2-ethylhexanoic acid, or a carboxylic acid.

7. The method of claim 1 wherein step a) comprises forming a dispersion comprising said liquid cyclohexane, said oxidant gas, and an oxidation catalyst slurry.

8. The method of claim 1 wherein said high shear device comprises a surface containing an oxidation catalyst.

9. The method of claim 1 wherein step a) comprises forming a precursor comprising a cyclohexyl hydroperoxide, a ketal, a acetal, 1,1' oxybiscyclohexane, a cyclohexyl ester of monocarboxylic and dicarboxylic acids, 7-oxabicycloheptane, 2-hydroxycyclohexanone, 2h-pyran-2-one tetrahydro, or 2-oxepanone.

10. The method of claim 1 wherein step b) comprises subjecting the dispersion to high shear.

\* \* \* \* \*